(12) United States Patent
Ladet et al.

(10) Patent No.: US 9,272,073 B2
(45) Date of Patent: *Mar. 1, 2016

(54) SURGICAL PATCH

(75) Inventors: Sébastien Ladet, Lyons (FR); Yves Bayon, Lyons (FR)

(73) Assignee: Sofradim Production (FR)

( * ) Notice: Subject to any disclaimer, the term of this patent is extended or adjusted under 35 U.S.C. 154(b) by 944 days.

This patent is subject to a terminal disclaimer.

(21) Appl. No.: 13/124,288

(22) PCT Filed: Oct. 16, 2009

(86) PCT No.: PCT/IB2009/007520
§ 371 (c)(1),
(2), (4) Date: Jul. 1, 2011

(87) PCT Pub. No.: WO2010/043980
PCT Pub. Date: Apr. 22, 2010

(65) Prior Publication Data
US 2011/0257666 A1    Oct. 20, 2011

Related U.S. Application Data

(60) Provisional application No. 61/106,354, filed on Oct. 17, 2008.

(51) Int. Cl.
| | | |
|---|---|---|
| *A61L 15/16* | (2006.01) | |
| *A61L 27/52* | (2006.01) | |
| *A61L 27/48* | (2006.01) | |
| *A61L 27/56* | (2006.01) | |

(52) U.S. Cl.
CPC ................. *A61L 27/52* (2013.01); *A61L 27/48* (2013.01); *A61L 27/56* (2013.01)

(58) Field of Classification Search
CPC .................................................... A61K 9/0024
USPC .................................................... 424/443–447
See application file for complete search history.

(56) References Cited

U.S. PATENT DOCUMENTS

| | | | |
|---|---|---|---|
| 5,201,745 A | 4/1993 | Tayot et al. | |
| 2002/0106409 A1* | 8/2002 | Sawhney et al. | 424/484 |
| 2003/0031697 A1 | 2/2003 | Chudzik et al. | |
| 2003/0199993 A1* | 10/2003 | Gellman et al. | 623/23.75 |
| 2005/0283255 A1* | 12/2005 | Geremakis et al. | 623/23.51 |
| 2007/0154513 A1* | 7/2007 | Atanasoska et al. | 424/423 |
| 2007/0260299 A1* | 11/2007 | Gagnieu | 623/1.1 |
| 2009/0068250 A1* | 3/2009 | Gravagna et al. | 424/426 |
| 2010/0016872 A1* | 1/2010 | Bayon et al. | 606/151 |

FOREIGN PATENT DOCUMENTS

| | | |
|---|---|---|
| EP | 2 177 239 | 4/2010 |
| EP | 2 179 753 | 4/2010 |

OTHER PUBLICATIONS

International Search Report PCT/IB2009/007520 dated Sep. 28, 2010.

* cited by examiner

*Primary Examiner* — Michael G Hartley
*Assistant Examiner* — Micah-Paul Young

(57) ABSTRACT

Multi-layer structures are useful as surgical patches.

19 Claims, 4 Drawing Sheets

SURGICAL PATCH

CROSS-REFERENCE TO RELATED APPLICATIONS

This application is a U.S. National Stage Application filed under 35 U.S.C. §371(a) of International Application No. PCT/IB2009/007520 filed Oct. 16, 2009, which claims the benefit of and priority to U.S. Provisional Application Ser. No. 61/106,354 filed Oct. 17, 2008, the entire contents of which are incorporated by reference herein.

TECHNICAL FIELD

The present disclosure relates to a patch or implant for visceral surgery. More particularly, it concerns methods and compositions useful for sealing and/or healing damaged visceral tissues. In certain aspects, the present patches can also minimize the formation of post-surgical adhesions.

BACKGROUND

Healing and sealing tissue wounds at the same time poses unique problems in visceral surgery. Devices (such as patches, meshes, plugs, etc.) that are used for the repair and/or regeneration of surrounding damaged visceral tissues need to be secured to tissue surrounding the wound. Sealing should be done without compromising the healing and by using the easiest techniques.

Sealing tissue wounds has been achieved via suturing or stapling to surrounding tissues. Alternative to suturing and stapling have been developed for closing openings in tissue such as incisions, wounds, anastomosis and fistulae. They include the use of i) biological glues such as fibrin sealant, gelatine-resorcinol glue and the glutaraldehyde albumin glue, ii) synthetic glues such as cyanoacrylate glues and iii) physical bonding techniques such as laser tissue welding to produce thermal effects to attach tissue surfaces, radio-frequency tissue welding or photosensitizer-assisted laser welding. Each of these prior techniques has certain drawbacks.

It would be desirable to provide an effective, safe, ready to use, affordable, and biocompatible device for tissue sealing which promotes healing of the wound.

SUMMARY

According to the present description, the expressions "porous layer", "porous substrate" and "porous matrix" have the same meaning and both designate a porous layer. By "porous layer" is meant, according to the present description, a layer having pores, voids, holes, channels, favorable to cell colonization. For example, the porous layer may be a sponge or a foam.

By "non porous layer", is meant, according to the present description, a layer being substantially free of any pores and having a substantially even surface, not favorable to cell colonization. For example, the non porous layer may be a film.

According to the present description, the expressions "implant", "patch", "surgical patch", "substitute", "sealant", have the same meaning and all designate the implant of the present application.

Surgical patches described herein are multi-layer structures that can, in embodiments, be self sticking and sealing and fully bioresorbable. In embodiments, the surgical patch is a bi-layered structure including a porous matrix layer (which optionally can be sub layered) that is loaded with a first hydrogel precursor and a layer made from a composition containing a second hydrogel precursor directly spread onto the porous matrix layer. In embodiments where the porous matrix layer is sub-layered, the porous matrix layer includes a first porous sublayer that is loaded with a first hydrogel precursor and a second porous sublayer that contains no hydrogel precursor onto which a layer of a second hydrogel precursor is directly spread. Generally, the first hydrogel precursor should be spatially separated from the second hydrogel precursor to prevent hydrogel precursors from reacting with each other until the implant is placed at the site of implantation and exposed to the physiological fluids of a patient.

In embodiments, the surgical patch is a tri-layered structure including a first porous matrix layer made, for example, of an oxidized collagen/chitosan mixture, containing a first hydrogel precursor. A first side of the porous matrix layer remains exposed and a second side of the porous matrix layer has adhered thereto a second, non porous layer, for example, a film made of collagen. A third layer made from a composition containing a second hydrogel precursor is spread directly onto the second, non porous layer. The second, non porous layer segregates the first and the second hydrogel precursor. Optionally, a non porous layer can be added onto the exposed side of the porous matrix layer. In addition, a reinforcement member optionally can be added between the porous matrix layer and the optional non porous layer on the exposed side thereof.

In yet other embodiments, the surgical patch is a tri-layered structure including a first porous matrix layer. A first side of the porous matrix layer remains exposed and a second side of the porous matrix layer has applied thereto a second layer containing a first hydrogel precursor. A third layer containing a second hydrogel precursor is applied to the second layer. As in the previous embodiments, a non porous layer optionally can be added onto the exposed side of the porous matrix layer and a reinforcement member optionally can be added between the porous matrix layer and the optional non porous layer on the exposed side thereof.

In embodiments, the layer containing the second hydrogel precursor can be applied as a uniform coating if self-sealing properties are requested over all the surface of the patch. Other coating patterns can be used for the layer containing the second hydrogel precursor in other embodiments to satisfy other adhesiveness expectations for the use of patches in visceral surgery.

Upon contact with tissue at the site of implantation, the implant will soak up physiological fluid. The second hydrogel precursor will be dissolved by the fluid. As the fluid wicks into and migrates across the implant, it will carry the dissolved second hydrogel precursor along through the implant. Eventually, the fluid will migrate through the implant sufficiently to reach the portion containing the first hydrogel precursor, thereby dissolving the first hydrogel precursor. The first and second hydrogel precursors will then react to form a biocompatible cross linked material, sticking the patch to the tissue at the site of implantation and sealing the defect. The biocompatible cross linked material produced by reaction of the first and second hydrogel precursors provides not only stickiness and sealant properties but also provides the implant with anti-adhesive properties between the defect and healthy surrounding tissues.

In embodiments, the thickness (indicated by "e" in the figures) of the fully processed implant, in the dry state, is in the range of about 0.2 mm to about 1 cm.

Methods for closing and healing visceral wall defects or incisions using the present surgical patch are also described. For example, the present surgical patch can improve the healing of gastro-intestinal anastomosis and be an effective approach to the management and prevention of fistula. Another example is the prevention by the present surgical patch of classic complications of polypectomy (e.g., bleeding and perforation). Another example is the use of embodiments of the present surgical patch that are reinforced with a mesh for the treatment of inguinal hernia and incisional hernia. An aspect of the invention is an implant comprising at least:

a porous layer, optionally a non porous layer, a first hydrogel precursor present in a layer selected from said porous layer and said non porous layer, and a second hydrogel precursor layer containing a second hydrogel precursor and defining a uniform or non uniform coating of at least one layer selected from said porous layer and said non porous layer.

In other words, an aspect of the invention is an implant having at least one of the following structures:

i) A structure comprising at least a porous layer, a first hydrogel precursor present in said porous layer, and a second hydrogel precursor layer containing a second hydrogel precursor and defining a uniform or non uniform coating of said porous layer, or ii) A structure comprising at least a porous layer, a non porous layer, a first hydrogel precursor present in a layer selected from said porous layer and said non porous layer, and a second hydrogel precursor layer containing a second hydrogel precursor and defining a uniform or non uniform coating of at least one layer selected from said porous layer and said non porous layer.

Said coating may form a non porous layer or a porous layer. For example, said coating defines a film. Said film may be uniform. In embodiments, the film containing the second hydrogel precursor comprises a uniform film over an entire surface of the porous layer.

Alternatively, said film is non uniform and defines patterns selected from stripes, pellets, peripheral outlines, and combinations thereof. In embodiments, the film containing the second hydrogel precursor is patterned on a surface of the porous layer.

In embodiments, the porous layer comprises at least one collagen which undergoes slow bioresorption in vivo and at least one collagen which undergoes rapid bioresorption in vivo. The porous layer may comprise oxidized collagen.

In embodiments, the porous layer comprises a mixture of oxidized collagen and glutaraldehyde (GTA) cross-linked collagen.

In embodiments, the porous layer comprises a self-crosslinked compound of a functionalized collagen and a glycosaminoglycan.

In embodiments, the porous layer comprises a first porous sublayer comprising the first hydrogel precursor secured to a second porous sublayer.

In embodiments, the implant comprises at least one non porous layer, said non porous layer being different from said second hydrogel precursor layer.

In embodiments, the non-porous layer is positioned between the porous layer and the film containing the second hydrogel precursor. In such an embodiment, the first hydrogel precursor may be present in the non porous layer.

Alternatively, the non-porous layer is applied to a first surface of the porous layer and the film containing the second hydrogel precursor is applied to a second surface of the porous layer.

In embodiments, the implant further comprises a second non-porous layer, said second non porous layer being different from said second hydrogel precursor layer.

The porous layer may be positioned between the non-porous layer and the second non-porous layer.

In embodiments, the implant further comprises a reinforcement member.

The reinforcement member may be a mesh.

The reinforcement member may be coated with a bioresorbable coating.

In embodiments, the reinforcement member contacts the non-porous layer.

In embodiments, the reinforcement member is positioned between the porous layer and the non-porous layer.

In embodiments, the first hydrogel precursor is present in the porous layer.

Another aspect of the invention is a method for preparing the implant above comprising:

providing a porous layer and optionally a non porous layer, a first hydrogel precursor being present in a layer selected from said porous layer and non porous layer, and applying a second hydrogel precursor to a layer selected from said porous layer and non porous layer to define a uniform or non uniform coating of said layer.

For example, the second hydrogel precursor is applied as a film.

In embodiments, the second hydrogel precursor is sprayed on said layer to define a non uniform film defining patterns selected from stripes, pellets, peripheral outlines, and combinations thereof.

The following clauses 1-33 define aspects of the invention:

1. An implant comprising:

a porous substrate comprising a first hydrogel precursor;

a film comprising a second hydrogel precursor, the second hydrogel precursor being spatially separated from the first hydrogel precursor; and a non-porous layer.

2. The implant of clause 1 wherein the porous substrate comprises at least one collagen which undergoes slow bioresorption in vivo and at least one collagen which undergoes rapid bioresorption in vivo.

3. The implant of clause 1 wherein the porous substrate comprises oxidized collagen.

4. The implant of clause 1 wherein the porous substrate comprises a self-crosslinked compound of a functionalized collagen and a glycosaminoglycan.

5. The implant of clause 1 wherein the porous substrate comprises a first porous sublayer comprising the first hydrogel precursor secured to a second porous sublayer.

6. The implant of clause 1 wherein the non-porous layer is positioned between the porous substrate and the film containing the second hydrogel precursor.

7. The implant of clause 1 wherein the non-porous layer is applied to a first surface of the porous substrate and the film containing the second hydrogel precursor is applied to a second surface of the porous substrate.

8. The implant of clause 1 further comprising a second non-porous layer.

9. The implant of clause 8 wherein the porous substrate is positioned between the non-porous layer and the second non-porous layer.

10. The implant of clause 1 further comprising a reinforcement member.

11. The implant of clause 10 wherein the porous substrate comprises a first porous sublayer comprising the first hydrogel precursor secured to a second porous sublayer.

12. The implant of clause 10 wherein the reinforcement member is a mesh.

13. The implant of clause 10 wherein the reinforcement member coated with a bioresorbable coating.

14. The implant of clause 10 wherein the reinforcement member contacts the non-porous layer.

15. The implant of clause 10 wherein the reinforcement member is positioned between the porous layer and the non-porous layer.

16. The implant of clause 8 further comprising a reinforcement member.

17. The implant of clause 9 further comprising a reinforcement member associated with the second non-porous layer.

18. The implant of clause 1 wherein the film containing the second hydrogel precursor comprises a uniform film over an entire surface of the porous layer.

19. The implant of clause 1 wherein the film containing the second hydrogel precursor is patterned on a surface of the porous layer.

20. A method comprising:
providing a porous substrate comprising a first hydrogel precursor;
applying a non-porous layer to a first side of the porous substrate; and
applying a film containing a second hydrogel precursor to the non-porous layer.

21. The implant of clause 20 wherein the porous substrate comprises a first porous sublayer comprising the first hydrogel precursor secured to a second porous sublayer.

22. The method of clause 20 further comprising applying a second non-porous layer to a second side of the porous substrate.

23. The method of clause 20 further comprising applying a mesh between the second non-porous layer and the porous substrate.

24. An implant comprising:
a porous substrate comprising a first hydrogel precursor;
a first non-porous layer applied to a first side of the porous substrate;
a film containing a second hydrogel precursor, the film being applied to the first non-porous layer;
a second non-porous layer applied to a second side of the porous substrate; and
a reinforcement member.

25. The implant of clause 24 wherein the porous substrate comprises a first porous sublayer comprising the first hydrogel precursor secured to a second porous sublayer.

26. The implant of clause 24 wherein the reinforcement member is a mesh

27. The implant of clause 24 wherein the reinforcement member is coated with a bioresorbable coating.

28. The implant of clause 24 wherein the reinforcement member is associated with the second non-porous layer.

29. The implant of clause 24 wherein the reinforcement member is positioned between the porous layer and the second non-porous layer.

30. An implant comprising:
a porous substrate;
a first non-porous layer applied to a first side of the porous substrate the first non-porous layer comprising a first hydrogel precursor; and
a film containing a second hydrogel precursor, the film being applied to the first non-porous layer.

31. The implant of clause 30 wherein the porous substrate comprises a first porous sublayer secured to a second porous sublayer.

32. The implant of clause 30 further comprising a reinforcement member.

33. The implant of clause 30 further comprising a second non-porous layer applied to a second side of the porous substrate.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiments given below, serve to explain the principles of the disclosure.

DETAILED DESCRIPTION OF PREFERRED EMBODIMENTS

Figure 1:
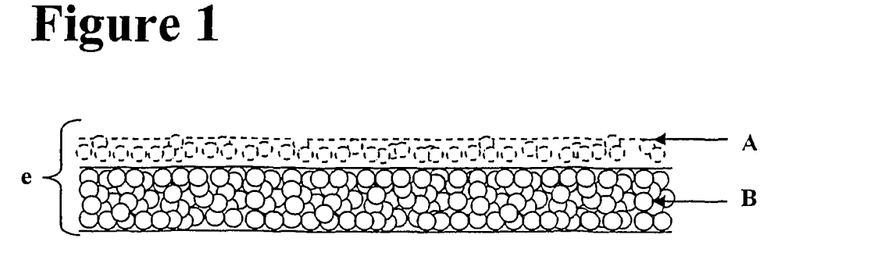
FIG. 1 schematically represents the structure of a porous matrix layer useful in embodiments in accordance with the present disclosure wherein sublayer A is a sublayer with lower polymer concentration than sublayer B which is loaded with a first hydrogel precursor. The layer containing the second hydrogel (2) precursor can be applied or spread over layer A which is free of hydrogel precursor as shown in FIG. 2A.

Surgical patches described herein are multi-layer structures. In the embodiment shown in FIG. 2A, for example, the surgical patch includes a porous matrix layer 1 (which optionally can be sub layered as shown in FIG. 1) that is loaded with a first hydrogel precursor and a layer 2 made from a composition containing a second hydrogel precursor directly spread onto porous matrix layer 1. In embodiments, the porous matrix layer is sub-layered. For example, as seen in FIG. 1, the porous matrix layer may include a first porous sublayer B that is loaded with a first hydrogel precursor and a second porous sublayer A that contains no hydrogel precursor onto which a layer of a second hydrogel precursor may be directly spread.

In embodiments, the surgical patch is a tri-layered structure. As shown in FIG. 2B, for example, the surgical patch may include a first porous matrix layer 1 made, for example, of a self-crosslinked oxidized collagen/chitosan mixture, containing a first hydrogel precursor. A first side of the porous matrix layer remains exposed and a second side of the porous matrix layer has adhered thereto a second, non porous layer 3, for example, a film made of collagen. A third layer 2 made from a composition containing a second hydrogel precursor is spread directly onto the second, non porous layer 3. The second, non porous layer 3 segregates the first and the second hydrogel precursor. Optionally, an additional non porous layer 4 can be added onto the exposed side of the porous matrix layer 1.

Figure 2A:
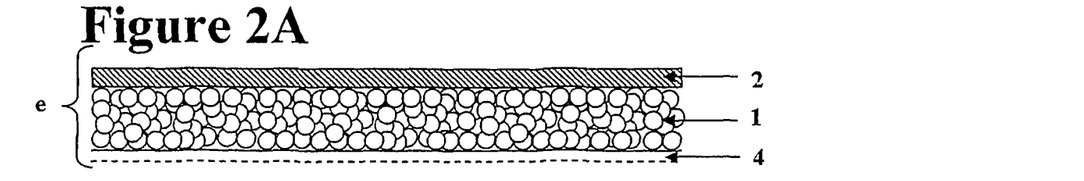
FIG. 2A schematically represents the structure of a two layer surgical patch in accordance with embodiments of the present disclosure, where the porous matrix (1) can be mono-layered or bi-layered as described in FIG. 1.
Figure 2B:
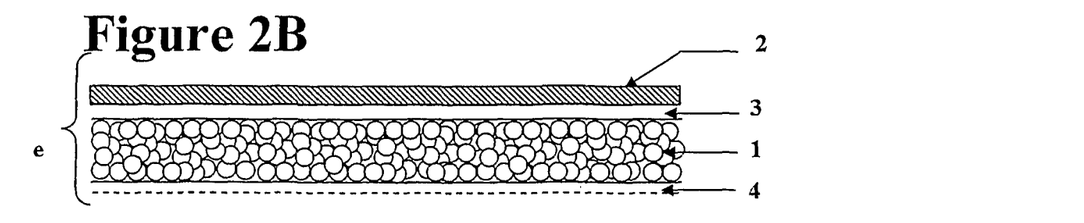
FIG. 2B schematically represents the structure of a three layer surgical patch in accordance with embodiments of the present disclosure.
Figure 2C:
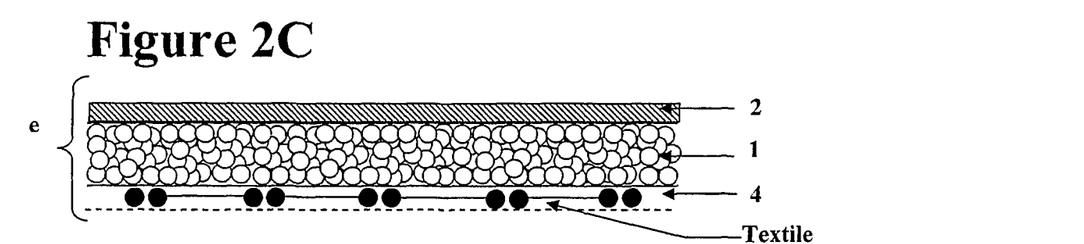
FIG. 2C schematically represents the structure of a three layer surgical patch in accordance with embodiments of the present disclosure with a reinforcement textile embedded within non porous layer (4) and porous layer (1).

In the embodiment shown in FIG. 2C, the surgical patch is a bi-layered structure that includes a first porous matrix layer 1 containing a first hydrogel precursor. A first side of the porous matrix layer remains exposed and a second side of the porous matrix layer has applied thereto a second layer 2, containing a second hydrogel precursor. As in the previous embodiments, a non porous layer 4 optionally can be added onto the exposed side of the porous matrix layer and a reinforcement member (labeled "textile" in FIG. 2C) optionally can be added between the porous matrix layer and the optional non porous layer on the exposed side thereof.

Figure 2D:
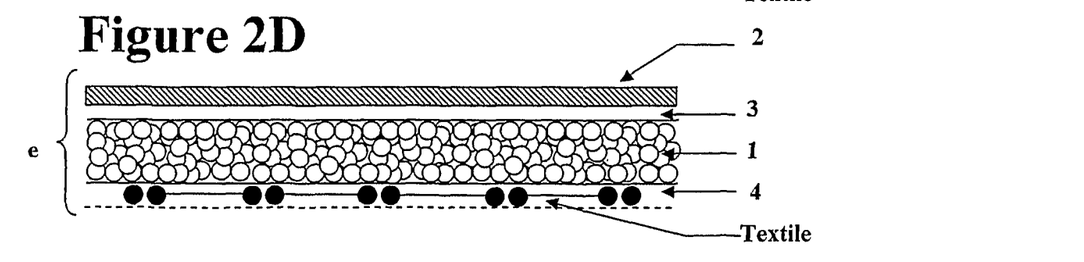
FIG. 2D schematically represents the structure of a four layer surgical patch in accordance with alternative embodiments of the present disclosure FIG. 2E schematically represents the structure of a three layer surgical patch in accordance with an alternative embodiment having the first hydrogel precursor within the non porous layer (3').

FIG. 2D shows an embodiment wherein the surgical patch is a tri-layered structure including a first porous matrix layer 1 containing a first hydrogel precursor. A first side of the porous matrix layer remains exposed and a second side of the porous matrix layer has applied thereto a second layer 3 as non porous layer based collagen and derivatives. A third, non porous layer 2 containing a second hydrogel precursor is applied to the second layer. As in the previous embodiments, a non porous layer optionally can be added onto the exposed side of the porous matrix layer and a reinforcement member optionally can be added between the porous matrix layer and the optional non porous layer on the exposed side thereof.

Figure 2E:
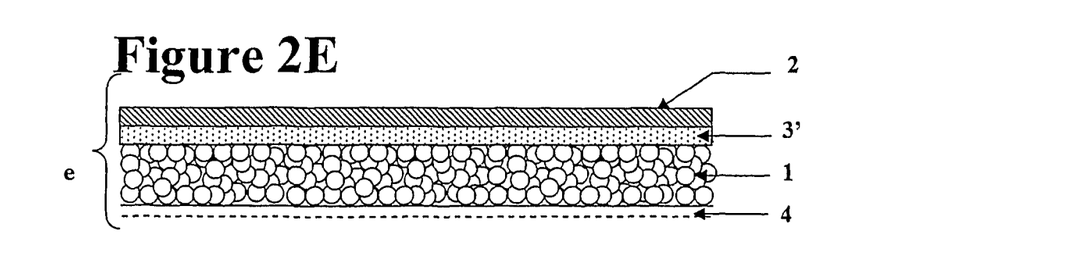

FIG. 2E shows an embodiment wherein the surgical patch is a tri-layered structure including a first porous matrix layer 1. A first side of the porous matrix layer remains exposed and a second side of the porous matrix layer has applied thereto a non porous second layer 3' containing a first hydrogel precursor. A third, layer 2 containing a second hydrogel precursor is applied to the second layer. As in the previous embodiments, a non porous layer optionally can be added onto the exposed side of the porous matrix layer and a reinforcement member (not shown) optionally can be added between the porous matrix layer and the optional non porous layer on the exposed side thereof.

Figure 4A:
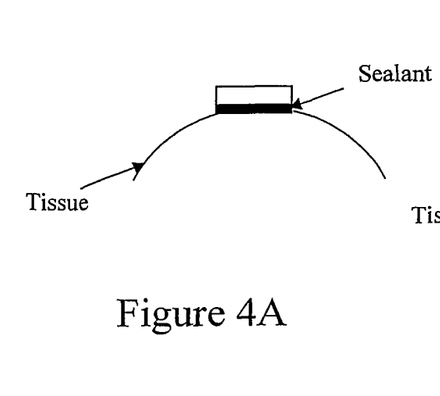
FIGS. 4A and B schematically illustrate use of surgical patches in accordance with embodiments of the present disclosure over small and large tissue defects, respectively.

During use, the implant can be oriented differently depending on the size of the defect (see FIG. 4A). In the cases of small defects the non-porous layer containing one of the hydrogel precursors is applied closer to the tissue and the porous matrix of the implant containing the other hydrogel precursor is positioned further from the tissue. This first case will create a watertight barrier over the defect to avoid any leakage of physiological fluid supported by a backing material providing a longer tissue support after the sealant will be degraded.

Figure 4B:
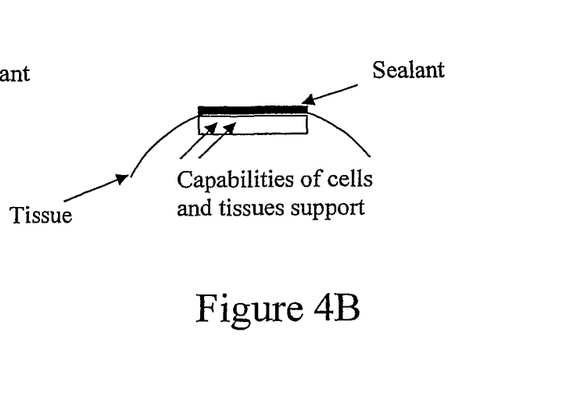

In the cases of bigger defects (see FIG. 4B) the portion of the porous matrix containing one of the hydrogel precursors is applied closer to the tissue and the non-porous layer of the implant containing the other hydrogel precursor is positioned further from the tissue. This second case will first bring the porous matrix directly onto the defect to support the tissue regeneration while the hydrogel barrier will be located over the matrix closing the defect but leaving free access for cell and tissue growth through the matrix.

Upon contact with tissue at the site of implantation, the implant will soak up physiological fluid. One of the two hydrogel precursors will be dissolved by the fluid. As the fluid wicks into and migrates across the implant, it will carry the dissolved hydrogel precursor along through the implant. Eventually, the fluid will migrate through the implant sufficiently to reach the portion containing the other hydrogel precursor, thereby dissolving that hydrogel precursor. The first and second hydrogel precursors will then react to form a biocompatible cross linked material, sticking the patch to the tissue at the site of implantation and sealing the defect.

Collagen and its Derivatives

Collagen is a naturally occurring protein exhibiting good biocompatibility. It is the major structural component of vertebrates, forming extracellular fibers or networks in practically every tissue of the body, including skin, bone, cartilage, and blood vessels. In medical devices, collagen provides a more physiological, isotropic environment that has been shown to promote the growth and function of different cell types, facilitating the rapid overgrowth of host tissue after implantation.

For the purpose of the present application, the term "collagen" is intended to mean any known collagen of porcine, bovine or human origin, including both natural or recombinant collagen, esterified collagen, for example methylated, ethylated or alternatively succinylated collagen, glycosylated collagen (e.g., collagen glycosylated with free amino saccharides/polysaccharides, collagen glycosylated with saccharides/polysaccharides comprising vicinal diols, collagen glycosylated with saccharides/polysaccharides comprising —$CH_x(NH_2)$—$CH_y(OH)$— chemical bonds), or one of its derivatives.

The term "gelatine" here includes commercial gelatine made of collagen which has been denatured by heating and in which the chains are at least partially hydrolyzed (molecular weight lower than 100 kDa).

The collagen used can be of human or animal origin. Some non-limiting examples include, type I porcine or bovine collagen, type I or type III human collagen or mixtures in any proportions of these types. In embodiments, the collagen or gelatine used is a porcine collagen.

The collagen can be functionalized by using any method known to those skilled in the art to provide pendant portions of the collagen with moieties which are capable of covalently bonding with the amino groups of a polymer such as collagen itself including its derivatives or modified glycosaminoglycan. Examples of such pendant moieties include aldehyde groups, sulfone groups, vinylsulfone groups, isocyanate groups, acid anhydride groups, epoxide groups, aziridine groups and episulfide groups. In addition, electrophilic groups such as —$CO_2N(COCH_2)_2$, —$CO_2N(COCH_2)_2$, —$CO_2H$, —$CHO$, —$CHOCH_2$, —$N{=}C{=}O$, —$SO_2CH{=}CH_2$, —$N(COCH)_2$, —S—S—$(C_5H_4N)$ may also be added to pendant chains of the collagen to allow covalent bonding to occur with the natural polymer showing amino group on their chains. Other suitable functional groups which may be added to collagen include groups of the following structures wherein X is Halogen and R is hydrogen or $C_1$ to $C_4$ alkyl:

In embodiments, the collagen may be modified through the addition of an oxidizing agent. Contacting collagen with an oxidizing agent creates oxidative cleavage along portions of the collagen thereby creating pendant aldehyde groups capable of reacting with the glycosaminoglycans. The oxidizing agent may be, for example, iodine, peroxide, periodic acid, hydrogen peroxide, a periodate, a compound containing periodate, sodium periodate, a diisocyanate compound, a halogen, a compound containing halogen, n-bromosuccinimide, a permanganate, a compound containing permanganate, ozone, a compound containing ozone, chromic acid, sulfuryl chloride, a sulfoxide, a selenoxide, an oxidizing enzyme (oxidase) and combinations thereof. In embodiments, the oxidizing agent is periodic acid.

Oxidized collagen can be fully degraded in vivo, after few weeks. It is obtained by the oxidation of a 3% (w/w) collagen solution by periodic acid (C=8 mM) at room temperature, during 3 hours. An example of the oxidative technique is described by Tardy et al. in U.S. Pat. No. 4,931,546, the entire content of which is herein incorporated by reference. Another technique for oxidized collagen is by oxidation of a 3% collagen solution by periodic acid, at a final concentration of 8 mM, during 3 hours, as described in U.S. Pat. No. 6,596,304, the entire content of which is herein incorporated by reference.

Oxidation of collagen forms aldehydes groups which allow cross-linking of the collagen with the amino groups of the chitosan. The cross-linked blend chitosan/collagen is less prone to the enzymatic degradation and then has a longer time of bioresorption in-vivo. Moreover the covalent bonds generated by the cross-linking decrease the solubility of the material in water at physiological pH and allow the formation of a tri-dimensional network which is a support for cell growth and differentiation and then tissue regeneration.

Glutaraldehyde (GTA) cross-linked collagen can be used in combination of oxidized collagen to bring tuneable in-vivo persistence according to the ratio of glutaraldehyde used to prepare the GTA cross-linked collagen.

Glycosaminoglycans and their Derivatives

The term "glycosaminoglycan" is intended to encompass complex polysaccharides having repeating units of either the same saccharide subunit or two or more different saccharide subunits. Some non-limiting examples of glycosaminoglycans include dermatan surfate, hyaluronic acid, the chondroitin sulfates, chitin, heparin, keratan surfate, keratosulfate, and derivatives thereof. Some non-limiting examples of derivatives may include partially and fully deacetylated versions of these compounds such as chitosan and deacetylated hyaluronic acid. The glycosaminoglycans may be extracted from a natural source, e.g., animal tissues such as squid pens and shrimp shells or vegetable sources such as mushrooms (e.g., "champigon de paris"), or they may be synthetically produced or synthesized by modified microorganisms such as bacteria.

In embodiments, the functionalized collagen may be combined with a glycosaminoglycan such as chitosan to crosslink and form covalent bonds. The glycosaminoglycan displays a degree of acetylation (DA) of about 0% to about 60%. In embodiments, the glycosaminoglycan displays a degree of acetylation (DA) of about 1% to about 50%. Samples of different degrees of acetylation can be obtained either by a heterogeneous deacetylation process or by a homogenous reacetylating process from a sample of a glycosaminoglycan that is fully deacetylated.

In embodiments, the glycosaminoglycan has a molecular weight ranging from about 100 to about 1,000,000 g/mol. In some embodiments, the glycosaminoglycan has a molecular weight ranging from about 162 (chitosan monomer) to about 1,000,000 g/mol. In addition, the glycosaminoglycan also displays a low polydisperity index between about 1.2 to about 1.8. In particularly useful embodiments, the glycosaminoglycan is chitosan. Nevertheless, the glycosaminoglycan may be a mixture of chitosans with different degrees of acetylation or a mixture of chitosans and other glycosaminoglycans, e.g. hyaluronic acid, with different degrees of acetylation and in which all glycosaminoglycan have the capability, i.e. have free amino groups, to be cross-linked to the oxidized collagen.

First and Second Hydrogel Precursors

The terms "first hydrogel precursor" and "second hydrogel precursor" each means a polymer, functional polymer, macromolecule, small molecule, or crosslinker that can take part in a reaction to form a network of crosslinked molecules, e.g., a hydrogel.

In embodiments, at least one of the first or second hydrogel precursors is a small molecule of about 1000 Da or less, and is referred to as a "crosslinker". The crosslinker preferably has a solubility of at least 1 g/100 mL in an aqueous solution. A crosslinked molecule may be crosslinked via an ionic or covalent bond, a physical force, or other attraction.

In embodiments, at least one of the first or second hydrogel precursors is a macromolecule, and is referred to as a "functional polymer". The macromolecule, when reacted in combination with a crosslinker, is preferably at least five to fifty times greater in molecular weight than the small molecule crosslinker and can be less than about 60,000 Da. In embodiments, a macromolecule that is seven to thirty times greater in molecular weight than the crosslinker is used and, in embodiments a macromolecule that is about ten to twenty times difference in weight is used. Further, a macromolecular molecular weight of 5,000 to 50,000 is useful. The term polymer, as used herein, means a molecule formed of at least three repeating groups.

Each of the first and second hydrogel precursors is multifunctional, meaning that it comprises two or more electrophilic or nucleophilic functional groups, such that, for example, a nucleophilic functional group on the first hydrogel precursor may react with an electrophilic functional group on the second hydrogel precursor to form a covalent bond. At least one of the first or second hydrogel precursors includes more than two functional groups, so that, as a result of electrophilic-nucleophilic reactions, the precursors combine to form crosslinked polymeric products. Such reactions are referred to as "crosslinking reactions".

In embodiments, each of the first and second hydrogel precursors includes only one category of functional groups, either only nucleophilic groups or only electrophilic functional groups, so long as both nucleophilic and electrophilic precursors are used in the crosslinking reaction. Thus, for example, if the first hydrogel precursor has nucleophilic functional groups such as amines, the second hydrogel precursor may have electrophilic functional groups such as N-hydroxysuccinimides. On the other hand, if first hydrogel precursor has electrophilic functional groups such as sulfosuccinimides, then the second hydrogel precursor may have nucleophilic functional groups such as amines or thiols. Thus, functional polymers such as proteins, poly(allyl amine), styrene sulfonic acid, or amine-terminated di- or multifunctional poly (ethylene glycol) ("PEG") can be used.

The first and second hydrogel precursors may have biologically inert and water soluble cores. When the core is a polymeric region that is water soluble, preferred polymers that may be used include: polyether, for example, polyalkylene oxides such as polyethylene glycol ("PEG"), polyethylene oxide ("PEO"), polyethylene oxide-co-polypropylene oxide ("PPO"), co-polyethylene oxide block or random copolymers, and polyvinyl alcohol ("PVA"); poly(vinyl pyrrolidinone) ("PVP"); poly(amino acids); poly (saccharides), such as dextran, chitosan, alginates, carboxymethylcellulose, oxidized cellulose, hydroxyethylcellulose, hydroxynethylcellulose, hyaluronic acid, and proteins such as albumin, collagen, casein, and gelatin. The polyethers and more particularly poly(oxyalkylenes) or poly(ethylene glycol) or polyethylene glycol are especially useful. When the core is small molecular in nature, any of a variety of hydrophilic functionalities can be used to make the first and second hydrogel precursors water soluble. For example, functional groups like hydroxyl, amine, sulfonate and carboxylate, which are water soluble, maybe used to make the precursor water soluble. In addition, N-hydroxysuccinimide ("NHS") ester of subaric acid is insoluble in water, but by adding a sulfonate group to the succinimide ring, the NHS ester of subaric acid may be made water soluble, without affecting its reactivity towards amine groups.

If it is desired that the biocompatible crosslinked polymer resulting from the reaction of the first and second hydrogel precursors be biodegradable or absorbable, one or more of the first and second hydrogel precursors may have biodegradable linkages present between the functional groups. The biodegradable linkage optionally also may serve as the water soluble core of one or more of the precursors. In the alternative, or in addition, the functional groups of the first and second hydrogel precursors may be chosen such that the product of the reaction between them results in a biodegradable linkage. For each approach, biodegradable linkages may be chosen such that the resulting biodegradable biocompatible crosslinked polymer will degrade, dissolve or be absorbed in a desired period of time. Preferably, biodegradable linkages are selected that degrade under physiological conditions into non-toxic products.

The biodegradable linkage may be chelates or chemically or enzymatically hydrolyzable or absorbable. Illustrative chemically hydrolyzable biodegradable linkages include polymers, copolymers and oligomers of glycolide, dl-lactide, l-lactide, caprolactone, dioxanone, and tritnethylene carbonate. Illustrative enzymatically hydrolyzable biodegradable linkages include peptidic linkages cleavable by metalloproteinases and collagenases. Additional illustrative biodegradable linkages include polymers and copolymers of poly(hydroxy acid)s, poly(orthocarbonate)s, poly(anhydride)s, poly(lactone)s, poly(amino acid)s, poly(carbonate)s, poly(saccharide)s and poly(phosphonate)s.

In embodiments, the biodegradable linkage may contain ester linkages. Some non-limiting examples include esters of succinic acid, glutaric acid, propionic acid, adipic acid, or amino acids, as well as carboxymethyl esters.

In embodiments, a multifunctional nucleophilic polymer such as trilysine may be used as a first hydrogel precursor and a multifunctional electrophilic polymer such as a multi-arm PEG functionalized with multiple NHS groups may be used as a second hydrogel precursor. The multi-arm PEG functionalized with multiple NHS groups can for example have four, six or eight arms and have a molecular weight of from about 5,000 to about 25,000. Many other examples of suitable first and second precursors are described in U.S. Pat. Nos. 6,152,943; 6,165,201; 6,179,862; 6,514,534; 6,566,406; 6,605,294; 6,673,093; 6,703,047; 6,818,018; 7,009,034; and 7,347,850, the entire content of each of which is incorporated herein by reference.

The first hydrogel precursor is applied to a first portion of the porous substrate and a second hydrogel precursor applied to a second portion of the porous substrate. For example, the precursors may be applied in a dry form, such as particulate matter or in a solid or semi-solid state such as a film, or foam. In embodiments, at least one of the first or second hydrogel precursors is applied to the porous matrix as a film. In embodiments, the first portion of the substrate having the first hydrogel precursor applied thereto is spatially separated from the second portion of the porous substrate having the second hydrogel precursor applied thereto. Having the first and second hydrogel precursors spatially separated from each other prevents them from reacting with each other until the implant is placed at the site of implantation and exposed to the physiological fluids of a patient.

Porous layer

The porous layer or matrix can be obtained by freeze drying a collagen suspension, resulting from the mixing of short term in-vivo persistence natural polymer and long term in-vivo persistence natural polymer.

A first example of such as a mixture is blend of oxidized collagen and glutaraldehyde (GTA) cross-linked collagen, at different concentrations to be further freeze dried to form a porous layer or matrix.

| | |
|---|---|
| (A) GTA cross-linked collagen content | 20%-100% (w/w total collagen) |
| (B) Oxidized collagen content | 80%-0% (w/w total collagen) |
| Total collagen concentration in the suspension | 0.2%-5% (w/w) |

The ratio (A/B) of concentration of the two collagen types may advantageously be between 1 and 5.

In embodiments, the composition from which the porous layer is formed contains from about 20 to about 100 percent by weight GTA cross-linked collagen and from about 0 to about 80 percent by weight Oxidized collagen. In embodiments, the total polymer concentration in the suspension used to form the porous layer is from about 0.5% w/w to about 2% w/w.

An alternative composition for the porous layer or matrix is obtained by freeze-drying a polymer solution containing one or more biodegradable and biocompatible polymers. Table 1 shows illustrative embodiments of polymer solutions suitable for use in forming the porous layer using a free-drying process.

TABLE 1

| | |
|---|---|
| (A) chitosan content | 0%-99% (w/w) |
| (B) Oxidized collagen content | 100%-1% (w/w) |
| Total polymer concentration in the suspension | 0.2%-5% (w/w) |

Where both chitosan and collagen are used, the weight ratio of chitosan to collagen in the composition used to form the porous layer may be from about 1:100 to 100:1, in embodiments, the weight ratio of chitosan to collagen is from about 1:10 to about 10:1, in yet other embodiments, the weight ratio of chitosan to collagen is about 1:1.

In embodiments, the composition from which the porous layer is formed contains from about 40 to about 90 percent by weight chitosan and from about 10 to about 60 percent by weight functionalized collagen. In embodiments, the total polymer concentration in the suspension used to form the porous layer is from about 0.5% w/w to about 2% w/w.

Combining Collagen and Glycosaminoglycan to Form the Porous Layer

Compounds useful in forming the porous layer of the implant of the present disclosure can be made by reacting a functionalized collagen with a glycosaminoglycan under conditions which cause the two components to self-cross link. As used herein, the term "self-crosslinked" when used in connection with the crosslinking of polymers means that two or more polymers are covalently bonded together by functionalities present on the polymers themselves without the use of a chemical cross linking agent. As an illustrative example, oxidized collagen (which contains aldehyde groups thereon) will covalently bond to chitosan (which contains amino groups thereon) without the addition of any separate chemical crosslinking agent to form a self-crosslinked compound. The two components may take the form of any solution, suspension, emulsion, semi-solid, or solid material capable of allowing the two-components to interact and self-crosslink.

In embodiments, each component is solubilized in an acceptable solvent such as deionized water to form two separate solutions. The two solutions may be combined to allow the two components to mix, self-crosslink and form the compounds described herein. In particular embodiments, the glycosaminoglycan is solubilized in deionized water with a stoechiometric amount of acid with a polymer concentration ranging from about 0.5% to about 10% (w/w). It is envisioned that the pH of the glycosaminoglycan solution can be adjusted if necessary between about 2 and about 7.5 depending on the degree of acetylation. The functionalized collagen is also solubilized in an acceptable solvent such as deionized water to a concentration ranging from about 0.5% to about 10% (w/w). It is also envisioned that the pH of the functionalized collagen solution may be adjusted between about 2 and about 7.5. The two components in solution are mixed to a final concentration of polymer comprising 0.5% and 20% (w/w). In embodiments, different proportions between the functionalized collagen and the glycosaminoglycan may be used. In particular embodiments, the glycosaminoglycan may be composed of a mixture of chitosans with different degrees of acetylation (DA). The chitosan having a degradation time in function with its degree of acetylation (Kurita et al., Carbohydrate polymers. Vol 42 pp. 19-21,200; Tomihata et al., Biomaterials. Vol 18 n° 7 pp. 567-575, 1997), the combination of slow and fast biodegradable chitosan is advantageous, for example, for progressive cell colonization of the porous layer. In fact, the degradation of the slow biodegradable oxidized collagen and chitosan with high DA, i.e. 35≤DA≤50, in vitro in the presence of viable cells and in vivo, helps to increase the interconnected porosity assisting in the regeneration of healthy native like tissue in the full thickness of the implant and the extent of tissue integration. In embodiments, molecules released from the controlled degradation of the biocomposite, for example oxidized collagen/chitosan, may advantageously confer to the implant highly interesting biological activities e.g. antimicrobial, anticancer, antioxidant, and immunostimulant effects, especially in the case of chitosan (Kim et al., Carbohydrate Polymers, Vol. 62, Issue 4, pp. 357-368, 2005) and may bring, in complement of the biocompatibility and biodegradability, bioactive properties to the medical devices. The biological properties of released chitosan oligopolymers enhance the tissue regeneration and extend the use of the implant, for example, to surgical sites with a high risk of contamination.

In embodiments, a combination of two solutions comprising an acidic solution of oxidized collagen and an acidic solution of chitosan with one or a mixture of several degrees of acetylation is used. The collagen is oxidized by the addition of periodic acid as the oxidizing agent and the chitosan solution is made acidic by the addition of hydrochloric acid. The mixture can be neutralized either with an alkaline vapour/solution or buffer solution with a pH greater than 7, leading to a cross-linked scaffold compatible for cell adhesion and proliferation.

Optionally, glycerine may be added to the solution used to form the porous layer. When present, the concentration of glycerine in the solution can typically be from about 2 to about 10 times less than that of the combined amount of collagen and glycosaminoglycan, in embodiments less than about one-third of the combined amount of collagen and glycosaminoglycan.

In embodiments, the first hydrogel precursor is loaded in the porous layer by incorporating the precursor in the polymer solution before freeze-drying. However where it is desired to segregate the first and the second hydrogel precursor the matrix bulk can be designed to preserve a volume free of both hydrogel precursors between the first portion with first hydrogel precursor and second portion with second hydrogel precursor as described in more detail below in connection with, for example, FIG. 1.

The porous layer can be from about 0.1 mm to about 3 mm thick in the dry state. In multi-layer embodiments, the porous layer can be from about 0.2 mm to about 1.5 mm thick in the dry state. The porous layer can have a density of from about 75 mg collagen/cm$^2$ to about 5 mg collagen/cm$^2$. The size of the pores in the porous layer can be from about 20 µm to about 300 µm, in embodiments from about 100 µm to about 200 µm.

After formation, the porous matrix can be compacted by using a press or any other appropriate means.

The Non-Porous Layer

When present, the non porous layer used in the implants of the present disclosure can be a film, for example a collagen film. Suitable collagen films can be made from non heated oxidized collagen, heated oxidized collagen, non oxidized heated collagen or combinations thereof. If heated oxidized collagen is used, the formulation of the film can be the formulations disclosed in U.S. Pat. No. 6,596,304, the entire disclosure of which is incorporated herein by reference.

Any materials which may enhance tissue repair, limit the risk of sepsis and modulate the mechanical properties (e.g., glycerol, 1-2 propandiol) of the film (swelling rate in water, tensile strength and the like) may be added during the preparation or in the film formulation.

The film may be further cross-linked by any known methods, when dried or during its drying.

Table 2 gives illustrative concentrations of collagen solutions useful in forming the non-porous layer.

TABLE 2

| | |
|---|---|
| Non heated oxidized collagen content | 0.1%-3% (w/w) |
| Heated Oxidized collagen content | 0.1%-6% (w/w) |
| Heated collagen content | 0.1%-6% (w/w) |

The non-porous layer may be prepared by pouring a collagen-containing solution onto a substantially flat support and distributing it evenly. This solution is left to gel by the removal of solvent and cooling.

Examples of solutions useful in forming the non-porous layer include from about 0.1 to about 3% w/w of non-heated oxidized collagen, up to 2% w/w polyethylene glycol and up to 1% w/w glycerol. In embodiments, solutions useful in forming the non-porous layer include from about 0.5 to about 1.5% w/w of non-heated oxidized collagen, from about 0.6 to about 0.9% w/w polyethylene glycol and from about 0.3 to about 0.6% w/w glycerol.

In the dry state, the resulting non-porous layer may contain from about 40 to about 100% w/w of non-heated oxidized collagen, up to 60% w/w polyethylene glycol and up to 20% w/w glycerol. In embodiments, the resulting non-porous layer contains from about 60 to about 90% w/w of non-heated oxidized collagen, from about 15 to about 30% w/w polyethylene glycol and from about 5 to about 15% w/w glycerol.

Other examples of solutions useful in forming the non-porous layer include from about 0.1 to about 3% w/w of heated oxidized collagen, from about 0.1 to about 3% w/w of heated collagen, up to 2% w/w polyethylene glycol and up to 1% w/w glycerol. In embodiments, solutions useful in forming the non-porous layer include from about 0.5 to about 1.5% w/w of non-heated oxidized collagen, from about 0.5 to about 1.5% w/w of heated collagen, from about 0.6 to about 0.9% w/w polyethylene glycol and from about 0.3 to about 0.6% w/w glycerol.

In the dry state, the resulting non-porous layer may contain from about 40 to about 100% w/w of heated oxidized collagen, about 40 to about 100% w/w of heated collagen, up to 60% w/w polyethylene glycol and up to 20% w/w glycerol. In embodiments, the resulting non-porous layer contains from about 60 to about 90% w/w of heated oxidised collagen, from about 60 to about 90% w/w of heated collagen, from about 15 to about 30% w/w polyethylene glycol and from about 5 to about 15% w/w glycerol.

In embodiments, at least one macromolecular hydrophilic additive that is chemically unreactive with the collagen may be added to the solution used to form the non-porous layer. "Chemically unreactive with the collagen" as used herein means a hydrophilic compound which is not likely to react with the collagen, notably which does not form covalent bonds with it during cross-linking.

The macromolecular hydrophilic additive advantageously has a molecular weight in excess of 3,000 Daltons, in embodiments from about 3,000 to about 20,000 Daltons. Illustrative examples of suitable macromolecular hydrophilic additives include polyalkylene glycols (such as polyethylene glycol), polysaccharides (e.g., starch, dextran and/or cellulose), oxidized polysaccharides, and mucopolysaccharides. It should of course be understood that combinations of macromolecular hydrophilic additives may be used. The concentration of hydrophilic additive(s) can typically be from about 2 to about 10 times less than that of the collagen.

Typically, the macromolecular hydrophilic additive is eliminated by diffusion through the non-porous layer, in a few days. The swelling of this material may advantageously promote degradation of a collagenic non-porous layer in less than a month.

Optionally, glycerine may be added to the solution used to form the non-porous layer. When present, the concentration of glycerine in the solution can typically be from about 2 to about 10 times less than that of the collagenic constituent, in embodiments less than about one-third of the collagen concentration.

The thickness of the non-porous layer is not critical, but typically can be less than about 100 µm thick, and in embodiments from about 15 µm to about 75 µm thick.

Second Hydrogel Precursor Layer

Figure 3A:
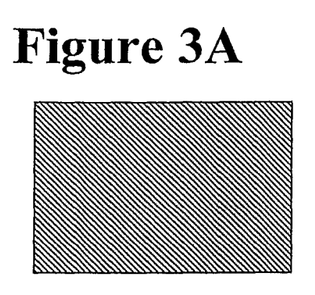
FIGS. 3A-D schematically represents illustrative coating patterns for the non-porous layer containing second hydrogel precursors useful in embodiments in accordance with the present disclosure.

The second hydrogel precursor may be applied to a layer of the implant using any suitable method known to those skilled in the art. For example, the second hydrogel precursor is applied to the implant as a film. In embodiments, the second hydrogel precursor may be spread directly onto the surface of the porous matrix by coating, hot melt spraying, or any other appropriate means. Alternatively, the second hydrogel precursor can be spread onto the non porous layer by the same methods. It is envisioned that a coating may be applied to the substrate in any desired concentration, dimension and configuration. In embodiments, the density of a film composed of the second hydrogel precursor is from about 5 mg/cm$^2$ to about 100 mg/cm$^2$. In embodiments, the second hydrogel precursor coating may penetrate the pores of the porous substrate. The coating may form a non-porous layer or a porous layer. The coating of the second hydrogel precursor can be as a uniform coating, in particular a uniform film over an entire surface of the porous layer (as seen in FIG. 3A), when the self-sealing properties are desired over the entire surface of the implant. In other embodiments, other coating patterns (such as the illustrative patterns shown in FIGS. 3B, 3C and 3D as non limiting examples) define a non uniform coating and can fulfil the adhesiveness expectations for the use of the implant in visceral surgery.

The advantage of being able to design different patterns of the second hydrogel precursor over the matrix surface is to balance the properties of the implant (sealing, adhesiveness and tissue support). These tunable properties thanks to the different patterns allow adapting the implant to the requirement of the surgical approach. Indeed, the uniform coating defined by the second hydrogel precursor layer, as shown on FIG. 3A, will preferably be used to promote a uniform hydrogel barrier (resulting from the cooperation of first hydrogel precursor and second hydrogel precursor) providing watertight closure in such application where leakages are the biggest concern such as in GI anastomoses (bowel, urethra etc.). In such a case, the uniform hydrogel barrier will momentarily delay the cellular/tissue integration.

Figure 3B:
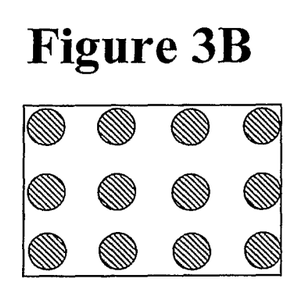
Figure 3C:
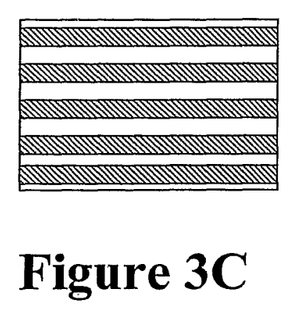
Figure 3D:
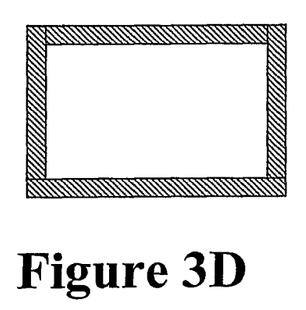

On the other hand, the multi shape patterns, such as the pellets, stripes, peripheral outlines, and combinations thereof, as respectively illustrated in FIGS. 3B, 3C and 3D, will induce a discontinuous hydrogel barrier over the matrix surface, once the implant is hydrated on the surface of the defect. The surface of the matrix free of hydrogel barrier would be able to support the cellular and tissue integration faster for a better healing when it is required such as in lung lobectomy to avoid air leakage or hernia repair. The non uniform coating patterns, such as stripes, pellets or peripheral outline may be obtained by spraying the second hydrogel precursor on the layer to be coated.

It is contemplated that the composition containing the second hydrogel precursor may contain additional, optional ingredients (such as, for example, viscosity modifiers, colorants, bioactive agents and the like) provided the additional components do not substantially impact the dissolving of the composition upon contact with physiological fluids and do not interfere with the chemical reaction of the first and second hydrogel precursors.

Reinforcement Member

The present patch may also include a reinforcement member. The reinforcement member may be positioned between the non-porous layer and the porous layer of the implant as illustrate in FIG. 2C. Alternatively, the reinforcement member may be positioned entirely within the non-porous layer. It is also envisioned that the reinforcement member may be positioned at the surface of one of the layers making up the multilayer implant and, in embodiments, may be positioned at an exterior surface of the multilayer implant.

Some suitable non-limiting examples of the reinforcement member include fabrics, meshes, monofilaments, multifilament braids, chopped fibers (sometimes referred to in the art as staple fibers) and combinations thereof.

Where the reinforcement member is a mesh, it may be prepared using any technique known to those skilled in the art, such as knitting, weaving, tatting, knipling or the like. Illustrative examples of suitable meshes include any of those that are presently commercially available for visceral tissue healing including the ones used for hernia. In embodiments where a mesh is used as the reinforcement member, the mesh will aid in affixing the composite to tissue without tearing of the porous or non-porous layers.

Where monofilaments or multifilament braids are used as the reinforcement member, the monofilaments or multifilament braids may be oriented in any desired manner. For example, the monofilaments or multifilament braids may be randomly positioned with respect to each other within the implant structure. As another example, the monofilaments or multifilament braids may be oriented in a common direction within the implant. In embodiments, monofilaments or multifilament braids are associated with both the porous layer and with the non-porous layer. In an illustrative embodiment of this type, the implant includes a first reinforcement member having a plurality of reinforcement members oriented in a first direction within the non-porous layer and a second reinforcement layer having a plurality of reinforcement members oriented in a second direction within the porous layer. In embodiments, the first and second directions may be substantially perpendicular to each other.

Where chopped fibers are used as the reinforcement member, the chopped fibers may be oriented in any desired manner. For example, the chopped fibers may be randomly oriented or may be oriented in a common direction. The chopped fibers can thus form a non-woven material, such as a mat or a felt. The chopped fibers may be joined together (e.g., by heat fusing) or they may be unattached to each other. The chopped fibers may be of any suitable length. For example, the chopped fibers may be from 0.1 mm to 100 mm in length, in embodiments, 0.4 mm to 50 mm in length. In an illustrative embodiment, the implant has randomly oriented chopped fibers that have not been previously fused together embedded within in the non-porous layer.

It is envisioned that the reinforcement member may be formed from any bioabsorbable, non-bioabsorbable, natural, and synthetic material previously described herein including derivatives, salts and combinations thereof. In particularly useful embodiments, the reinforcement member may be made from a non-bioabsorbable material to provide long term flexible tissue support. In embodiments, the reinforcement member is a surgical mesh made from polypropylene or polylactic acid. In addition polyethylene materials may also be incorporated into the implant described herein to add stiffness. Where monofilaments or multifilament braids are used as the reinforcement member, any commercially available suture material may advantageously be employed as the reinforcement member.

The knitted mesh used as a reinforcement member of the patch is within the purview of those skilled in the art and include, but are not limited to the herein described meshes.

A reinforcement member suitable for the present implant may be a textile. The textile is either knitted, woven or non-woven. It is obtained with permanent biocompatible materials (e.g. polyesters, polypropylene), biodegradable biocompatible materials (e.g. polylactic acid, polyglycolic acid, oxidized cellulose) or with a combination at any proportion of both permanent and biodegradable materials. The textile is designed in such a way to be enough porous and to show appropriate mechanical properties to support the wound healing. The pore size is from about 1 mm to about 5 mm, the density from about 10 g/m$^2$ to about 200 g/m$^2$. The porosity, defined by the relative volume of pores within the mesh, is about from about 20% to about 98%.

Coating of the Reinforcement Member

In one embodiment of the implant of the invention, at least a part of the yarns constituting said mesh are coated with a bioresorbable coating. For example, said coating can be chosen from collagen, chitosan, polysaccharides or mixtures thereof. The polysaccharides can be chosen from hyaluronic acid, alginic acid, polyglucuronic acid, chitosan, starch, soluble cellulose derivatives, and mixtures thereof. Such a yarn coating makes it possible in particular to eliminate any possible crevice within the knit of the implant according to the invention, for example where the yarns cross each other, such crevices being liable to create sites where bacteria or inflammatory cells develop. Such an implant thus makes it possible to reduce the risks of inflammation and sepsis, the bioresorbable coating making the accessible surface of the knit completely smooth and thus preventing the installation of undesirable bacteria and/or microorganisms and/or inflammatory cells.

In one embodiment, at least part of the yarns constituting the mesh is covered with a bioresorbable coating. The bioresorbable coating can be chosen from oxidized collagen, glutaraldehyde-crosslinked collagen, collagen cross-linked with bifunctional or trifunctional glycidyl ethers, carbodiimides, acyl azides, divinylsulphone, collagen crosslinked by UV-, beta- or gamma-irradiation or by heat treatment, and mixtures thereof. The assembly of yarns constituting said knit can be covered with such a coating. For example, the coating is made of collagen. In particular, a collagen chosen from the group comprising oxidized collagen, glutaraldehyde-crosslinked collagen and mixtures thereof can be used for such a coating.

In one embodiment, the yarns of the knit are covered, at least in part by coating the knit in a solution or suspension of collagen, in one step or in several steps. A coating step comprises the actual coating of the knit with the collagen and the drying of the knit. The collagen deposited on the yarns can be crosslinked with glutaraldehyde after each application, as many times as the total number of coating cycles. Preferably, the yarns are covered by carrying out two or three successive coating cycles.

In another embodiment, the bioresorbable coating can be chosen from polysaccharides including hyaluronic acid, alginic acid, polyglucuronic acid, chitosan, starch, soluble cellulose derivatives and mixtures thereof.

In another embodiment, before it is coated with the bioresorbable coating described above, the knit suitable for the implant of the invention can be subjected to a surface treatment in order to render it more hydrophilic and thus promote the deposition of the collagen and/or the polysaccharides mentioned above on the knit. The surface treatment can be carried out according to any process known to those skilled in the art. Such a coating makes it possible to reduce the surface of the knit accessible to bacteria and to inflammatory cells. The risks of inflammation and sepsis are thus reduced.

Alternatively, the mesh may be processed by a surface treatment (e.g. plasma treatments) for enhanced properties. For example, a $N_2$ plasma treatment may give a more hydrophilic and/or a positively charged mesh at its surface. Such a treatment will facilitate the mesh coating with collagens and glycosaminoglycans.

Optional Bioactive Agents

In some embodiments, at least one bioactive agent may be combined with the present surgical patch and/or any of the individual components (the porous layer or the optional non-porous layer) used to construct the present surgical patch. In these embodiments, the present dural repair material can also serve as a vehicle for delivery of the bioactive agent. The term "bioactive agent", as used herein, is used in its broadest sense and includes any substance or mixture of substances that have clinical use. Consequently, bioactive agents may or may not have pharmacological activity per se, e.g., a dye, or fragrance. Alternatively a bioactive agent could be any agent which provides a therapeutic or prophylactic effect, a compound that affects or participates in tissue growth, cell growth, cell differentiation, an anti-adhesive compound, a compound that may be able to invoke a biological action such as an immune response, or could play any other role in one or more biological processes. It is envisioned that the bioactive agent may be applied to the present surgical patch in any suitable form of matter, e.g., films, powders, liquids, gels and the like.

Examples of classes of bioactive agents which may be utilized in accordance with the present disclosure include anti-adhesives, antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, and enzymes. It is also intended that combinations of bioactive agents may be used.

Anti-adhesive agents can be used to prevent adhesions from forming between the present surgical patch and the surrounding tissues opposite the target tissue. In addition, anti-adhesive agents may be used to prevent adhesions from forming between the present surgical patch and the packaging material. Some examples of these agents include, but are not limited to poly(vinyl pyrrolidone), carboxymethyl cellulose, hyaluronic acid, polyethylene oxide, poly vinyl alcohols and combinations thereof.

Suitable antimicrobial agents which may be included as a bioactive agent in the surgical patch of the present disclosure include triclosan, also known as 2,4,4'-trichloro-2'-hydroxydiphenyl ether, chlorhexidine and its salts, including chlorhexidine acetate, chlorhexidine gluconate, chlorhexidine hydrochloride, and chlorhexidine sulfate, silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine, polymyxin, tetracycline, aminoglycosides, such as tobramycin and gentamicin, rifampicin, bacitracin, neomycin, chloramphenicol, miconazole, quinolones such as oxolinic acid, norfloxacin, nalidixic acid, pefloxacin, enoxacin and ciprofloxacin, penicillins such as oxacillin and pipracil, nonoxynol 9, fusidic acid, cephalosporins, and combinations thereof. In addition, antimicrobial proteins and peptides such as bovine lactoferrin and lactoferricin B and antimicrobial polysaccharides such as fucans and derivatives may be included as a bioactive agent in the surgical patch of the present disclosure.

Other bioactive agents which may be included as a bioactive agent in the surgical patch in accordance with the present disclosure include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-parkinson agents such as L-dopa; anti-spasmodics; anticholinergic agents (e.g. oxybutynin); antitussives; bronchodilators; cardiovascular agents such as coronary vasodilators and nitroglycerin; alkaloids; analgesics; narcotics such as codeine, dihydrocodeinone, meperidine, morphine and the like; nonnarcotics such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; estrogens; antibacterials; antibiotics; anti-fungals; anti-virals; anticoagulants; anticonvulsants; antidepressants; antihistamines; and immunological agents.

Other examples of suitable bioactive agents which may be included in the present surgical patch include viruses and cells, peptides, polypeptides and proteins, analogs, muteins, and active fragments thereof, such as immunoglobulins, antibodies, cytokines (e.g. lymphokines, monokines, chemokines), blood clotting factors, hemopoietic factors, interleukins (IL-2, IL-3, IL-4, IL-6), interferons ((3-IFN, (a-IFN and y-IFN), erythropoietin, nucleases, tumor necrosis factor, colony stimulating factors (e.g., GCSF, GM-CSF, MCSF), insulin, anti-tumor agents and tumor suppressors, blood proteins, gonadotropins (e.g., FSH, LH, CG, etc.), hormones and hormone analogs (e.g., growth hormone), vaccines (e.g., tumoral, bacterial and viral antigens); somatostatin; antigens; blood coagulation factors; growth factors (e.g., nerve growth factor, insulin-like growth factor); protein inhibitors, protein antagonists, and protein agonists; nucleic acids, such as antisense molecules, DNA and RNA; oligonucleotides; polynucleotides; and ribozymes.

EXAMPLES

The following non-limiting examples show possible combinations of materials useful in preparing implants in accordance with embodiments of the present disclosure.

Example 1

Preparation of Coated Mesh Reinforcement Member

A knitted isoelastic, multifilament polyglycolic acid mesh reinforcement member is coated in a solution of porcine collagen at 0.8% w/v, by soaking it in the solution, spin-drying it and leaving it to dry under a laminar flow. This cycle of processes is repeated up to two times in order to obtain covering of the yarns.

The collagen used is porcine collagen type I, extracted from porcine dermis by solubilization at acidic pH or by digestion with pepsin, and purified by saline precipitations according to known techniques.

Dry collagen fibres obtained by precipitation of an acid solution of collagen by adding NaCl, and then washing and drying of the precipitate obtained with aqueous solutions of acetone having an increasing concentration of 80% to 100%, are preferably used.

At the end of the coating, the collagen deposited on the knit is crosslinked with glutaraldehyde at 0.5% w/v (aqueous solution of glutaraldehyde at 25%, w/v, sold by the company Fluka), at neutral pH (pH between 6.5 and 7.5), for 2 hours, and is then reduced with sodium borohydride. The reagents used are removed by washing the knit with several water baths. The crosslinking of the collagen deposited on the mesh can alternatively be carried out at the end of each coating cycle.

Preparation of Glutaraldehyde-Crosslinked Collagen

Porcine collagen is solubilized in water at a final concentration of 1% w/v. The collagen used is porcine collagen type I, extracted from porcine dermis by solubilization at acidic pH or by digestion with pepsin, and purified by saline precipitations according to known techniques.

Dry collagen fibres obtained by precipitation of an acid solution of collagen by adding NaCl, and then washing and drying the precipitate obtained with aqueous solutions of acetone having an increasing concentration of 80% to 100%, are preferably used.

The solution of collagen at 1% w/v is then neutralized by adding sodium phosphate at a final concentration of 20 mM. The final pH of the suspension was measured at between 6.5 and 7.5.

Glutaraldehyde (aqueous solution of glutaraldehyde at 25%, w/v, sold by the company Fluka) is then added to the suspension at a final concentration of 0.5% w/v. After two hours at ambient temperature, collagen fibres are recovered by filtration of the suspension through a nylon mesh. These fibres are then treated with sodium borohydride for at least two hours until the yellow coloration of the fibres has completely disappeared. The white fibres thus obtained are washed and neutralized at pH 6.5-7.5, and dried by removing the water with acetone. The acetone residues are then evaporated off.

Preparation of Oxidized Collagen

A solution of porcine collagen at 3% w/v is oxidized with periodic acid at a final concentration of 8 mM, at ambient temperature, according to Example 4 of U.S. Pat. No. 6,596,304.

Preparation of the porous matrix

A suspension of collagen is prepared by mixing 60.5 g of glutaraldehyde-crosslinked collagen suspension at 1% w/w and 60.5 g oxidized collagen solution at 1% w/w. The pH of the collagen suspension thus obtained is then increased to 7 and tri-lysine is added to the blend as a first hydrogel precursor at a final concentration of 2.5 mg/ml. Then the suspension poured in a 17×12 cm box and is lyophilized according to the following method: freezing is carried out as rapidly as possible, by decreasing the temperature of the product from 8° C. to −45° C., generally in less than 2 hours. Primary desiccation is initiated at −45° C., at a pressure of from 0.1 to 0.5 mbar. During this step, the temperature is gradually increased, with successive slopes and plateaux, to +30° C. The lyophilization ends with secondary desiccation, at +30° C., for 1 to 24 hours. Preferably, the vacuum at the end of secondary desiccation is between 0.005 and 0.2 mbar. The total lyophilization time is from 18 to 72 hours. If necessary a supplementary step of neutralization can be add. In this case another step of lyophilization may be required.

Alternate Method for Preparation of the Porous Matrix 60.5 g of chitosan solution (DA 2.5%) and 60.5 g of non heated, oxidized collagen solution (1% w/w) are mixed at pH 3.5. Glycerol (0.121 g) is added to the solution under stirring for 10 minutes. The pH of the solution is adjusted to 4.5 and tri-lysine is added to the blend as a first hydrogel precursor at a final concentration of 3 mg/ml. Finally the solution is centrifuged. The solution is poured in 17×12 cm box and is lyophilized according to the following method: freezing is carried out as rapidly as possible, by decreasing the temperature of the product from 8° C. to −45° C., generally in less than 2 hours. Primary desiccation is initiated at −45° C., at a pressure of from 0.1 to 0.5 mbar. During this step, the temperature is gradually increased, with successive slopes and plateaux, to +30° C. The lyophilization ends with secondary desiccation, at +30° C., for 1 to 24 hours. Preferably, the vacuum at the end of secondary desiccation is between 0.005 and 0.2 mbar. The total lyophilization time is from 18 to 72 hours.

The matrix is compressed to obtain a thickness between of 0.1 and 1 mm. Then the porous matrix is neutralized in 1M NaOH solution for 20 minutes. After a complete wash in sterile water, until the pH 7, the matrix is freeze dried again.

Method for Preparation of a Sub-Layered Porous Matrix

A composition destined to form a first sublayer is prepared by mixing a first hydrogel precursor within a polymer solution, with a polymer concentration C1. This composition is poured into a container. The pH of the polymer/hydrogel precursor blend is adjusted between 7 and 8 in order to allow an optimal reactivity of both hydrogel precursors, ie of first hydrogel precursor and second hydrogel precursor, as described below. A second solution destined to form the second sublayer is prepared having a polymer concentration C2 lower than C1. This second solution is poured over the first solution layer. The difference of viscosity of the two solutions avoids the mixing of the two different layers to preserve to bi-layered structure. The two sublayers of the porous matrix are simultaneously freeze dried to provide a sub-layered porous matrix layer. If necessary, the porous matrix layer may be neutralized using a basic solution/vapour or buffer solution in order that the dissociation state of the first hydrogel precursor will be adapted for optimal reactivity with the second hydrogel precursor.

Alternate Method for Preparation of a Sub-Layered Porous Matrix 40.5 g of chitosan solution (DA 2.5%) and 40.5 g of non heated, oxidized collagen (also referred to CXN hereinafter) solution (1% w/w) are mixed at pH 3.5 under stirring for 10 minutes. The pH of the solution is adjusted to 4.5 and tri-lysine is added to the blend as a first hydrogel precursor with a concentration of 3 mg/ml. Finally the solution is centrifuged. The solution is poured in box and is destined to form one of the sublayers.

Then, 20 g of chitosan solution (DA 2.5%) and 20 g of CXN solution (0.5% w/w) are mixed at pH 3.5. Then the pH is modified to 4.5. This lower concentration solution is gently applied over the first sublayer and the whole is lyophilized as described above. The total lyophilization time is from 18 to 72 hours.

Then the porous matrix is neutralized within water/alcohol mixture 5/95 w/w with sodium hydroxyde 0.5N for 5 min and freeze dried again.

Application of a Film to Exposed Face of the Implant

The porous matrix obtained in one of the above illustrative processes is subsequently coated with an oxidized collagen film as described in Example 2 of U.S. Pat. No. 6,391,939, the entire contents of which are incorporated herein by this reference.

A concentrated sterile solution of PEG 4000 (polyethylene glycol having a molecular weight of 4000 D, for example sold by the company Fluka under the trade name PEG 4000) and glycerol is added to a solution of oxidized collagen (obtained by oxidation of porcine collagen) at 3% w/v, so as to obtain a final composition having a PEG 4000 concentration of 1% w/v and a glycerol concentration of 0.6% w/v. The pH of the solution is adjusted to 7.0 by adding a concentrated solution of sodium hydroxide. The volume of the solution is then adjusted with sterile water so as to obtain final concentrations of collagen, of PEG 4000 and of glycerol of 2.7% w/v, 0.9% w/v and 0.54% w/v, respectively. The solution is then spread out so as to form a thin sheet with a density of 0.133 g/cm² on a flat hydrophobic support of polyvinyl chloride or polystyrene type. The surface is then exposed to a stream of sterile air at ambient temperature for just less than one hour and the coated mesh reinforcement member is applied over the gelling layer. The porous matrix obtained above is then applied carefully to the gelled composite of textile (ie reinforcement member) and oxidized collagen above. The whole is exposed to a stream of sterile air at ambient temperature until complete evaporation in about 18 hours.

Optional Application of a Second Film to the Other Face of the Implant

The film-mesh-porous matrix composite produced above, is then applied on a thin collagen coating to provide a reinforced film-porous matrix-film sandwich.

A concentrated sterile solution of PEG 4000 (polyethylene glycol having a molecular weight of 4000 D, for example sold by the company Fluka under the trade name PEG 4000) and glycerol is added to a solution of oxidized collagen (obtained by oxidation of porcine collagen) at 3% w/v, so as to obtain a final composition having a PEG 4000 concentration of 1% w/v and a glycerol concentration of 0.6% w/v. The pH of the solution is adjusted to 7.0 by adding a concentrated solution of sodium hydroxide. The volume of the solution is then adjusted with sterile water so as to obtain final concentrations of collagen, of PEG 4000 and of glycerol of 1% w/v, 0.9% w/v and 0.54% w/v, respectively. The solution is then spread out so as to form a thin sheet with a density of 0.05 g/cm$^2$ on a flat hydrophobic support of polyvinyl chloride or polystyrene type. The surface is then exposed to a stream of sterile air at ambient temperature for two hours. The porous face of the film-mesh-porous matrix composite obtained above is then applied carefully to the gelled layer of oxidized collagen above. The whole is exposed to a stream of sterile air at ambient temperature until complete evaporation in about 18 hours. The resulting product is a reinforced film-porous matrix-film sandwich as shown schematically in FIG. 2D.

Coating of the Film with Second Hydrogel Precursor

A thin uniform layer of melted PEG-succinimidyl glutarate (the second hydrogel precursor) with a density of 25 mg/cm$^2$ is formed on hot surface at the temperature of 50° C. Then the reinforced film-porous matrix-film sandwich produced above is directly applied with the film side free of textile onto the melted PEG. The final composite is exposed to a stream of sterile air at ambient temperature for 15 min.

Alternatively, the second hydrogel precursor could be sprayed on the film side free of textile to define a non uniform film defining patterns selected from stripes, pellets, peripheral outlines, and combinations thereof.

Example 2

Preparation of the Porous Matrix

A suspension of collagen is prepared by mixing 60.5 g of glutaraldehyde-crosslinked collagen suspension at 1% w/w and 60.5 g oxidized collagen solution at 1% w/w. The pH of the collagen suspension thus obtained is then increased to 7 and tri-lysine is added to the blend as a first hydrogel precursor at a final concentration of 2.5 mg/ml. Then the suspension poured in a 17×12 cm box and is further lyophilized according to the following method: freezing is carried out as rapidly as possible, by decreasing the temperature of the product from 8° C. to −45° C., generally in less than 2 hours. Primary desiccation is initiated at −45° C., at a pressure of from 0.1 to 0.5 mbar. During this step, the temperature is gradually increased, with successive slopes and plateaux, to +30° C. The lyophilization ends with secondary desiccation, at +30° C., for 1 to 24 hours. Preferably, the vacuum at the end of secondary desiccation is between 0.005 and 0.2 mbar. The total lyophilization time is from 18 to 72 hours.

Alternate Method for Preparation of the Porous Matrix 60.5 g of chitosan solution (DA 2.5%) and 60.5 g of non heated, oxidized collagen solution (1% w/w) are mixed at pH 3.5. 0.121 g of glycerol is added to the solution under stirring for 10 minutes. The pH of the solution is adjusted to 4.5 and tri-lysine is added to the blend as a first hydrogel precursor at a final concentration of 3 mg/ml. Finally the solution is centrifuged. The solution is poured in a 17×12 cm box and is further lyophilized according to the following method: freezing is carried out as rapidly as possible, by decreasing the temperature of the product from 8° C. to −45° C., generally in less than 2 hours. Primary desiccation is initiated at −45° C., at a pressure of from 0.1 to 0.5 mbar. During this step, the temperature is gradually increased, with successive slopes and plateaux, to +30° C. The lyophilization ends with secondary desiccation, at +30° C., for 1 to 24 hours. Preferably, the vacuum at the end of secondary desiccation is between 0.005 and 0.2 mbar. The total lyophilization time is from 18 to 72 hours.

Then the porous matrix is neutralized in 1M NaOH solution for 20 minutes. After a complete wash in sterile water, until the pH 7, the matrix is freeze dried again.

Preparation of the Bi-Layered Porous Matrix

Collagen Blend:

A suspension of collagen is prepared by mixing 20.5 g of glutaraldehyde-crosslinked collagen suspension at 1% w/w and 20.5 g oxidized collagen solution at 1% w/w. The pH of the collagen suspension thus obtained is then increased to 7 and poured in the box and then freeze overnight. Then a second suspension of collagen is prepared by mixing 40.5 g of glutaraldehyde-crosslinked collagen suspension at 1% w/w and 40.5 g oxidized collagen solution at 1% w/w. The pH of the collagen suspension thus obtained is then increased to 7 and tri-lysine is added to the blend as a first hydrogel precursor at a final concentration of 2.5 mg/ml. Then the second suspension poured over the frozen first layer lyophilized according to the following method: freezing is carried out as rapidly as possible, by decreasing the temperature of the product from 8° C. to −45° C., generally in less than 2 hours. Primary desiccation is initiated at −45° C., at a pressure of from 0.1 to 0.5 mbar. During this step, the temperature is gradually increased, with successive slopes and plateaux, to +30° C. The lyophilization ends with secondary desiccation, at +30° C., for 1 to 24 hours. Preferably, the vacuum at the end of secondary desiccation is between 0.005 and 0.2 mbar. The total lyophilization time is from 18 to 72 hours.

Collagen and Chitosan Case:

20.5 g of chitosan solution (DA 2.5%) and 20.5 g of non heated, oxidized collagen solution (1.5% w/w) are mixed at pH 3.5. The pH of the solution is adjusted to 4.5, poured in 17×12 cm box and stored at 4° C. during preparation of the second layer. 40.5 g of chitosan solution (DA 2.5%) and 40.5 g of non heated, oxidized collagen solution (0.8% w/w) are mixed at pH 3.5, then pH of the solution is adjusted to 4.5 and tri-lysine is added to the blend as a first hydrogel precursor at a final concentration of 3 mg/ml. Thenafter the second solution is pourred over the first layer having a higher viscosity avoiding the mix between the two layers. The bilayerd mixture is further lyophilized according to the following method: freezing is carried out as rapidly as possible, by decreasing the temperature of the product from 8° C. to −45° C., generally in less than 2 hours. Primary desiccation is initiated at −45° C., at a pressure of from 0.1 to 0.5 mbar. During this step, the temperature is gradually increased, with successive slopes and plateaux, to +30° C. The lyophilisation ends with secondary desiccation, at +30° C., for 1 to 24 hours. Preferably, the vacuum at the end of secondary desiccation is between 0.005 and 0.2 mbar. The total lyophilization time is from 18 to 72 hours.

Then the porous matrix is neutralized in 1M NaOH solution for 20 minutes. After a complete wash in sterile water, until the pH 7, the matrix is freeze dried again.

Application of a Film to One Face of the Implant

The porous matrix obtained above is subsequently coated with an oxidized collagen film as described in Example 2 of U.S. Pat. No. 6,391,939.

A concentrated sterile solution of PEG 4000 (polyethylene glycol having a molecular weight of 4000 D, for example sold by the company Fluka under the trade name PEG 4000) and glycerol is added to a solution of oxidized collagen (obtained by oxidation of porcine collagen) at 3% w/v, so as to obtain a final composition having a PEG 4000 concentration of 1% w/v and a glycerol concentration of 0.6% w/v. The pH of the solution is adjusted to 7.0 by adding a concentrated solution of sodium hydroxide. The volume of the solution is then adjusted with sterile water so as to obtain final concentrations of collagen, of PEG 4000 and of glycerol of 1% w/v, 0.9% w/v and 0.54% w/v, respectively. The solution is then spread out so as to form a thin sheet with a density of 0.05 g/cm$^2$ on a flat hydrophobic support of polyvinyl chloride or polystyrene type. The surface is then exposed to a stream of sterile air at ambient temperature for just less than one hour and the textile part, if textile is present like described in Example 1, is applied over the gelling layer. The matrix obtained above is then applied carefully to the gelled composite of textile and oxidized collagen above. The whole is exposed to a stream of sterile air at ambient temperature until complete evaporation in about 18 hours. The result is a porous matrix-collagen film composite.

Coating with Second Hydrogel Precursor as Described in FIG. 2A:

A thin uniform layer of melting PEG-succinimidyl glutarate (the second hydrogel precursor) with a density of 25 mg/cm$^2$ is formed on hot surface at the temperature of 50° C. Then the free side of the sublayer of the porous matrix which is without hydrogel precursors is directly applied on the melted PEG. The final composite is exposed to a stream of sterile air at ambient temperature for 15 min.

Alternatively, the second hydrogel precursor could be sprayed on the free side of the sublayer of the porous matrix which is without hydrogel precursors to define a non uniform film defining patterns selected from stripes, pellets, peripheral outlines, and combinations thereof.

Example 3

Preparation of the Porous Matrix

A suspension of collagen is prepared by mixing 60.5 g of glutaraldehyde-crosslinked collagen suspension at 1% w/w and 60.5 g oxidized collagen solution at 1% w/w. The pH of the collagen suspension thus obtained is then increased to 7. Then the suspension is poured in a 17×12 cm box and is further lyophilized according to the following method: freezing is carried out as rapidly as possible, by decreasing the temperature of the product from 8° C. to −45° C., generally in less than 2 hours. Primary desiccation is initiated at −45° C., at a pressure of from 0.1 to 0.5 mbar. During this step, the temperature is gradually increased, with successive slopes and plateaux, to +30° C. The lyophilization ends with secondary desiccation, at +30° C., for 1 to 24 hours. Preferably, the vacuum at the end of secondary desiccation is between 0.005 and 0.2 mbar. The total lyophilization time is from 18 to 72 hours.

Alternate Method for the Preparation of the Porous Matrix 60.5 g of chitosan solution (DA 2.5%) and 60.5 g of non heated, oxidized collagen solution (1% w/w) are mixed at pH 3.5. 0.121 g of glycerol is added to the solution under stirring for 10 minutes. The pH of the solution is adjusted to 4.5 and then centrifuged. The solution is poured in box and is further lyophilized according to the following method: freezing is carried out as rapidly as possible, by decreasing the temperature of the product from 8° C. to −45° C., generally in less than 2 hours. Primary desiccation is initiated at −45° C., at a pressure of from 0.1 to 0.5 mbar. During this step, the temperature is gradually increased, with successive slopes and plateaux, to +30° C. The lyophilization ends with secondary desiccation, at +30° C., for 1 to 24 hours. Preferably, the vacuum at the end of secondary desiccation is between 0.005 and 0.2 mbar. The total lyophilization time is from 18 to 72 hours.

The matrix is compressed to obtain a thickness between of 0.1 and 1 mm. Then the porous matrix is neutralized in 1M NaOH solution for 20 minutes. After a complete wash in sterile water, until the pH 7, the matrix is freeze dried again.

Application of a Film to One Face of the Implant

The porous matrix obtained above is subsequently coated with an oxidized collagen film as described in Example 2 of U.S. Pat. No. 6,391,939.

A concentrated sterile solution of PEG 4000 (polyethylene glycol having a molecular weight of 4000 D, for example sold by the company Fluka under the trade name PEG 4000) and glycerol is added to a solution of oxidized collagen (obtained by oxidation of porcine collagen) at 3% w/v, so as to obtain a final composition having a PEG 4000 concentration of 1% w/v and a glycerol concentration of 0.6% w/v. The pH of the solution is adjusted to 7.0 by adding a concentrated solution of sodium hydroxide. The volume of the solution is then adjusted with sterile water so as to obtain final concentrations of collagen, of PEG 4000 and of glycerol of 1% w/v, 0.9% w/v and 0.54% w/v, respectively. At this step an amount of tri-lysine is added within the collagen solution as a first hydrogel precursor in order to obtain a final concentration of 2.5 mg/ml. The solution is then spread out so as to form a thin sheet with a density of 0.05 g/cm$^2$ on a flat hydrophobic support of polyvinyl chloride or polystyrene type. The surface is then exposed to a stream of sterile air at ambient temperature for just less than one hour and the textile part, if textile is present like described in Example 1, is applied over the gelling layer. The porous matrix obtained above is then applied carefully to the gelled composite of textile and oxidized collagen above. The whole is exposed to a stream of sterile air at ambient temperature until complete evaporation in about 18 hours. The result is a porous matrix-collagen film composite.

Coating of the Film with Second Hydrogel Precursor as Describe in FIG. 2B

A thin uniform layer of melting PEG-succinimidyl glutarate (the second hydrogel precursor) with a density of 25 mg/cm$^2$ is formed on hot surface at the temperature of 50° C. Then the film side of the porous matrix-collagen film composite is directly applied on the melted PEG. The whole is exposed to a stream of sterile air at ambient temperature for 15 min.

Alternatively, the second hydrogel precursor could be sprayed on the film side of the porous matrix-collagen film composite to define a non uniform film defining patterns selected from stripes, pellets, peripheral outlines, and combinations thereof.

Example 4

Preparation of the Porous Matrix 40.5 g of chitosan solution (DA 2.5%) and 40.5 g of non heated, oxidized collagen solution (1% w/w) are mixed at pH 3.5. 0.121 g of glycerol is added to the solution under stirring for 10 minutes. The pH of the solution is adjusted to 4.5 and tri-lysine is added to the blend with a concentration of 3 mg/ml. Finally the solution is centrifuged. The solution is poured in box in order to form the sublayer B. Then, 20 g of chitosan solution (DA 2.5%) and 20 g of CXN solution (0.5% w/w) are mixed at pH 3.5. This lower concentration solution is gently applied over the sublayer B to form a sublayer A and the whole is further lyophilized according to the following method: freezing is carried out as rapidly as possible, by decreasing the temperature of the product from 8° C. to −45° C., generally in less than 2 hours. Primary desiccation is initiated at −45° C., at a pressure of from 0.1 to 0.5 mbar.

During this step, the temperature is gradually increased, with successive slopes and plateaux, to +30° C. The lyophilization ends with secondary desiccation, at +30° C., for 1 to 24 hours. Preferably, the vacuum at the end of secondary desiccation is between 0.005 and 0.2 mbar. The total lyophilization time is from 18 to 72 hours.

Then the porous matrix is neutralized within ammonia vapor for 3 hours and placed in ventilated oven at 50° C. during 48 h.

Coating of the Matrix with Second Hydrogel Precursor:

A thin uniform layer of melting PEG-succinimidyl glutarate (the second hydrogel precursor) with a density of 15 mg/cm$^2$ is formed on hot surface at the temperature of 50° C. Then the sublayer A of the porous matrix produced above is directly applied on the melted PEG. The whole is exposed to a stream of sterile air at ambient temperature for 15 min.

Alternatively, the second hydrogel precursor could be sprayed on the sublayer A of the porous matrix to define a non uniform film defining patterns selected from stripes, pellets, peripheral outlines, and combinations thereof.

It will be understood that various modifications may be made to the embodiments disclosed herein. For example, more than two precursors may be employed in forming the implant. As another example, the first and second precursors may each be applied to the porous substrate as a film. Thus, those skilled in the art will envision other modifications within the scope and spirit of the claims.

What is claimed is:

1. An implant comprising:
    a porous layer comprising collagen,
    a first hydrogel precursor;
    a second hydrogel precursor layer containing a second hydrogel precursor,
    optionally a non porous layer comprising collagen,
    wherein the first hydrogel precursor is present in a layer selected from said porous layer and said non porous layer, and
    the second hydrogel precursor layer defines a coating on at least one layer selected from said porous layer and said non porous layer, the coating defining a non-uniform film pattern selected from stripes, pellets, peripheral outlines, and combinations thereof,
    wherein the first and second hydrogel precursors are maintained in their respective layers separate from each other until the implant is placed at a site of implantation and exposed to physiological fluids thereby reacting the first and second hydrogel precursors with each other to form a self-sticking biocompatible cross-linked material which sticks the implant to tissue at the site of implantation.

2. The implant of claim 1, wherein the porous layer comprises at least one collagen which undergoes slow bioresorption in vivo and at least one collagen which undergoes rapid bioresorption in vivo.

3. The implant of claim 1 wherein the porous layer comprises oxidized collagen.

4. The implant of claim 1, wherein the porous layer comprises a mixture of oxidized collagen and glutaraldehyde (GTA) cross-linked collagen.

5. The implant of claim 1, wherein the porous layer comprises a self-crosslinked compound of a functionalized collagen and a glycosaminoglycan.

6. The implant of claim 1, wherein the porous layer comprises a first porous sublayer comprising the first hydrogel precursor secured to a second porous sublayer.

7. The implant of claim 1, comprising at least one non porous layer, said non porous layer being different from said second hydrogel precursor layer.

8. The implant of claim 7, wherein the non-porous layer is positioned between the porous layer and the second hydrogel precursor layer.

9. The implant of claim 7, wherein the non-porous layer is applied to a first surface of the porous layer and the second hydrogel precursor layer is applied to a second surface of the porous layer.

10. The implant of claim 8, further comprising a second non-porous layer, said second non porous layer being different from said second hydrogel precursor layer.

11. The implant of claim 10, wherein the porous layer is positioned between the non-porous layer and the second non-porous layer.

12. The implant of claim 7, further comprising a reinforcement member.

13. The implant of claim 12, wherein the reinforcement member is a mesh.

14. The implant of claim 12, wherein the reinforcement member is coated with a bioresorbable coating.

15. The implant of claim 12, wherein the reinforcement member contacts the non-porous layer.

16. The implant of claim 12, wherein the reinforcement member is positioned between the porous layer and the non-porous layer.

17. The implant of claim 1, wherein the first hydrogel precursor is present in the porous layer.

18. The implant of claim 8, wherein the first hydrogel precursor is present in the non porous layer.

19. A method for preparing an implant comprising:
    providing a porous layer comprising collagen and optionally a non porous layer comprising collagen, a first hydrogel precursor being present in a layer selected from said porous layer and said non porous layer, and
    applying a second hydrogel precursor to a layer selected from said porous layer and said non porous layer to define a coating on said layer, the coating defining a non-uniform film pattern selected from stripes, pellets, peripheral outlines, and combinations thereof,
    such that the first and second hydrogel precursors are maintained in their respective layers separate from each other until the implant is placed at a site of implantation and exposed to physiological fluids thereby reacting the first and second hydrogel precursors with each other to form a self-sticking biocompatible cross-linked material which sticks the implant to tissue at the site of implantation.

* * * * *